United States Patent [19]

Emanuel et al.

[11] 4,332,934
[45] Jun. 1, 1982

[54] 13-(1-OXYL-2,2,6,6-TETRAMETHYLPIPERY-LIDENYL-4)HYDRAZONE RUBOMYCIN HYDROCHLORIDE WITH A PARAMAGNETIC CENTER AND A METHOD OF PRODUCING SAME

[76] Inventors: Nikolai M. Emanuel, Vorobievskoe shosse, 2B, kv. 44, Moscow; Nina P. Konovalova, Noginsky raion, p/o Chernogolovka, ulitsa Tretya, 3, kv. 1, Moskovskaya oblast; Leonard S. Povarov, ulitsa Krasikova, 19, kv. 28, Moscow; Anatoly B. Shapiro, B. Koptevsky proezd, 4, kv. 37, Moscow; Raisa F. Dyachkovskaya, Vorobievskoe shosse, 2b, kv. 9, Moscow; Valentina I. Suskina, ulitsa Ulyanova, 49, korpus 1, kv. 58, Moscow; Ljudmila K. Denisova, Noginsky raion, p/o Chernogolovka, Shkolny bulvar, 1b, kv. 100, Moskovskaya oblast, all of U.S.S.R.

[21] Appl. No.: 192,964

[22] Filed: Oct. 2, 1980

[30] Foreign Application Priority Data

Mar. 24, 1980 [SU] U.S.S.R. ............................. 2893526

[51] Int. Cl.³ .......................................... C07H 15/24
[52] U.S. Cl. ..................................... 536/6.4; 424/180
[58] Field of Search ................... 536/4, 17 R, 17 A; 424/180

[56] References Cited

FOREIGN PATENT DOCUMENTS 2557537 7/1976 Fed. Rep. of Germany .

Primary Examiner—Blondel Hazel
Attorney, Agent, or Firm—Ladas & Parry

[57] ABSTRACT

A novel chemical compound is 13-(1-oxo-2,2,6,6-tetramethylpiperylidenyl-4)hydrazone rubomycin hydrochloride, featuring a paramagnetic center and corresponding to the formula

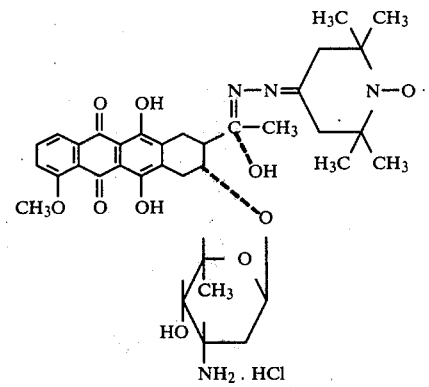

The novel compound is formed by reacting rubomycin base with 1-oxo-2,2,6,6-piperidone-4-hydrazone.

The novel compound is capable of inhibiting the growth of malignant tumors and is applicable in medicine; it features reduced toxicity, higher antitumor activity and a wider range of action as compared to known rubomycin derivatives.

2 Claims, 1 Drawing Figure

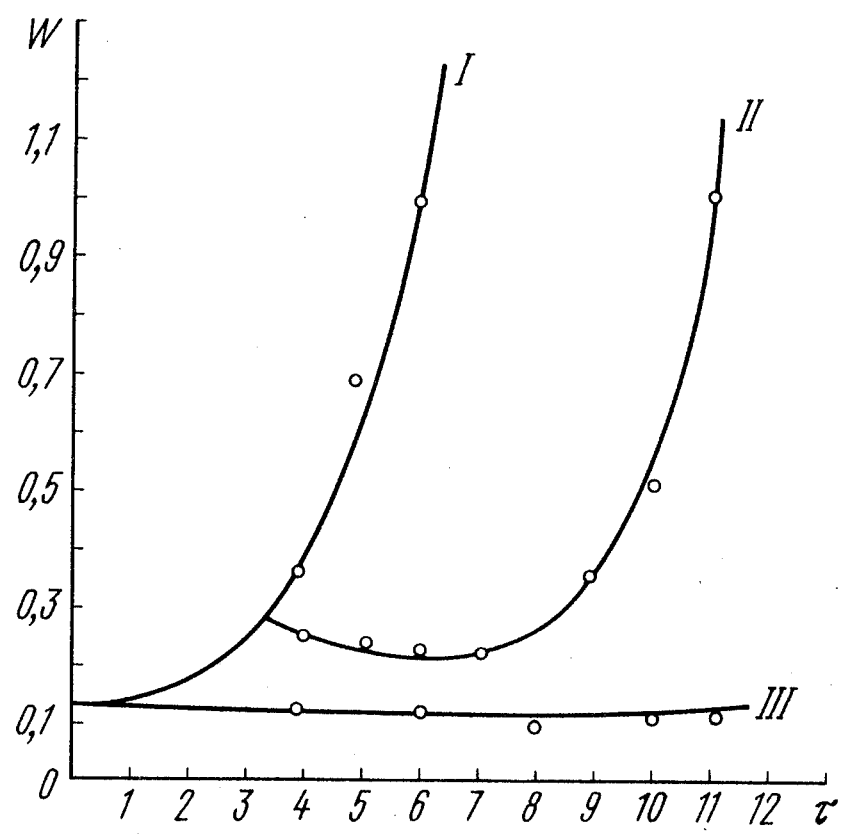

13-(1-OXYL-2,2,6,6-TETRAMETHYLPIPERYLIDE-NYL-4)HYDRAZONE RUBOMYCIN HYDROCHLORIDE WITH A PARAMAGNETIC CENTER AND A METHOD OF PRODUCING SAME

APPLICABILITY OF THE INVENTION

This invention relates generally to the chemopharmaceutical industry that is, to biologically active compounds featuring antitumor activity, and has particular reference to rubomycin derivatives.

BACKGROUND OF THE INVENTION

Antibiotic rubomycins were known in medicine heretofore (cf. an article "Physicochemical properties of an antitumor antibiotic Rubomycin produced by Actinomyces coeruleorubidus" by M. G. Brazhnikova, N. V. Konstantinova et al., in a journal "Antibiotiki" (Antibiotics) No. 9, 1966, Meditsina Publishers, Moscow, pp. 763 through 766/in Russian/).

The aforementioned antibiotic is also referred to in international practice as Daunorubicin. Synonyms of rubomycin are also Daunomycin and Rubidomycin.

At present rubomycin is in widespread clinical use for treatment of acute leukoses, chorionepithelioma of the uterus, and tumoral reticulosis (cf. "Clinical chemotherapy of neoplastic diseases" by N. I. Perevodchikova, issued in 1976 by Meditsina Publishers, Moscow, p.37/in Russian/).

However, rubomycin produces also various untoward effects, viz., it is cardiotoxic, inhibits hemopoiesis, has but a restricted range of action and inadequate antitumor activity.

There are also known some rubomycin derivatives, i.e., substituted hydrazones of daunorubicin (rubomycin) of the following general formula

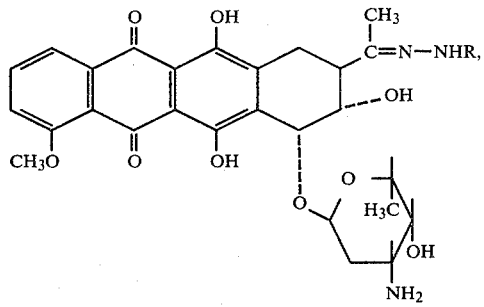

where R is $COCH_3$, $COC_2H_5$, $COCH(CH_3)_2$, $CO(CH_2)_{14}CH_3$, $COC_6H_5$, $COC_6H_4N$, $COC_6H_4(-pOCH_3)$, or CHO, said derivatives featuring antitumor activity.

The majority of these compounds retains the activity of daunorubicin, some of them being less toxic than the latter. The best among these compounds proves to be daunorubicin benzoylhydrazone (rubidazone, where R is $COC_6H_5$), which is less cardiotoxic (cf. French Pat. No. 1,578,722 published in 1967, Class C07d).

SUMMARY OF THE INVENTION

The present invention aims at providing a novel, more efficacious compound featuring reduced toxicity, higher antitumor activity and a wider range of action as compared with the known compounds of the same purpose.

According to the aforementioned and other objects the present invention provides a novel rubomycin derivative, viz., 13-(1-oxo-2,2,6,6-tetramethylpiperylidenyl-4)hydrazone rubomycin hydrochloride with a paramagnetic centre, of the formula

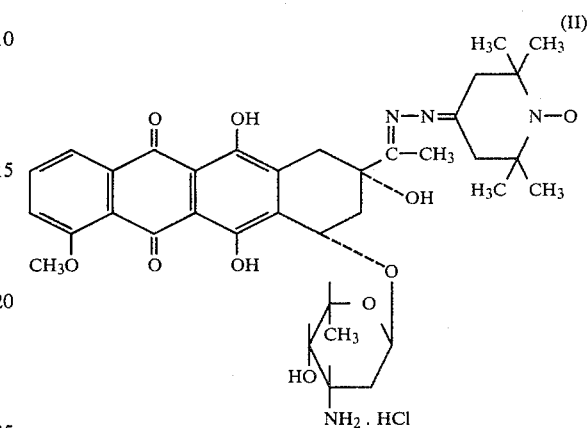

As to its chemical structure this compound is an asymmetrical bis-hydrazone, which may also be considered as an asymmetrical azine and is therefore a novel type of rubomycin derivative that has not heretofore been described in literature. Another specific feature of the compound in question is the presence of a paramagnetic centre in its molecule.

The aforesaid novel compound has tentatively been named "Ruboxyl".

The compound being claimed features antitumor activity; it is found to inhibit the growth of tumors and is applicable in oncological practice for treating malignant blood diseases and tumors of various localizations. In addition, this compound is less toxic, features higher antitumor activity and a wider range of action as compared with the aforementioned known compounds. Comparative data on toxicity and antitumor activity of the present compound and of the known ones are tabulated hereinbelow.

The presence of a paramagnetic centre in the present compound makes it possible to carry out pharmacokinetic studies by the electron paramagnetic resonance (EPR) method. This in turn enables one to trace the accumulation of the preparation containing the present compound as an active principle in and its excretion from the organs and tissues of man and animals without resorting to the synthesis of a tracer compound, which is in fact an active isotope.

The novel compound with a paramagnetic centre is essentially a red crystalline substance soluble in water, ethanol and chloroform. The EPR spectrum is a triplet with $\alpha N$ equal to 15.6 Gs. M.p.=175° or 176° C. (with decomposition). $[n]_D^{20} + 264°$.

Found, percent: C, 59.02; 58.80; H, 6.42; 6.57; N, 7.60, 7.55; $C_{36}H_{45}N_4O_{10}\cdot HCl$: Calculated, percent: C, 59.20; H, 6.36; N, 7.68.

IR spectrum (KBr): no band ($\nu=1720$ cm$^{-1}$) characteristic of the C=O group with $C_{13}$ of rubomycin; the band having $\nu=1680^{-1}$ is present, characteristic of the C=N group.

Another subject of the present invention is a method of producing 13-(1-oxo-2,2,6,6-tetramethylpiperylidenyl-4) hydrazone rubomycin hydrochloride. Rubomycin hydrochloride is treated with an alkali agent to form the rubomycin base, followed by an interreaction of the rubomycin base with 1-oxo-2,2,6,6-tetramethylpiperidone-4hydrazone (in a respective molar ratio of 1:1.5 to 2) in a chloroform-methanol medium with a respective volumetric ratio of 8:1 in the presence of acetic acid in a fourfold molar excess with respect to the rubomycin base, at 20° to 25° C., the formed precipitate is separated, while the solution remaining after precipitate separation and containing the reaction product is treated with an alcoholic solution of hydrogen chloride in a twofold molar excess with respect to the rubomycin base, whereupon the resultant end product is made to precipitate with diethyl ether.

DETAILED DESCRIPTION OF THE INVENTION

Interreaction of the rubomycin base with 1-oxo-2,2,6,6-tetramethylpiperidone-4 hydrazine and further treatment of the resultant reaction product with hydrogen chloride proceed according to the following scheme:

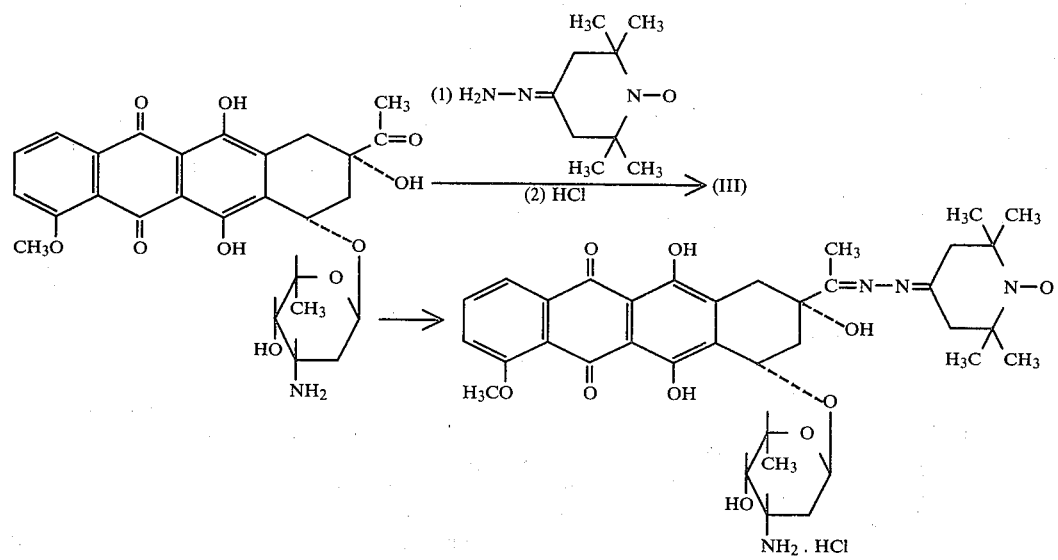

Below is a specific exemplary synthesis of the novel compound disclosed herein, viz, 13-(1-oxo-2,2,6,6-tetramethylpiperylidenyl-4)hydrazone rubomycin hydroxide.

EXAMPLE

Added to 1.5 g (2.66 mmole) rubomycin hydrochloride solution in 50 ml water is 25 ml 0.2 N solution of $Na_2CO_3$, the rubomycin base is extracted with 250 ml chloroform, the extract is evaporation concentrated in vacuum down to 75 ml, whereupon added thereto are 0.9 g (4.9 mmole) 1-oxyl-2,2,6,6-tetramethylpiperidone-4 hydrazone, 0.5 ml acetic acid and 10 ml methanol. The solution is allowed to stand for two days at 20° to 25° C., the precipitate is filtered off, added to the filtrate is 10 ml 0.6 N HCl solution in methanol, and the end product is made to precipitate with diethyl ether.

The yield is 800 mg 13-(1-oxyl-2,2,6,6-tetramethylpiperylidenyl-4)hydrazone rubomycin hydrochloride, which makes up 41.5 percent of the starting rubomycin hydrochloride.

In a chloroform-methanol-water system (volume ratio 13:6:1) Rf for the resultant end product equals 0.64, for the rubomycin hydrochloride Rf equals 0.55. Potency against Bacillus mycoides makes up 26 percent of that of the rubomycin hydrochloride.

The compound being claimed has been tested experimentally for biological potency on animals, acute and chronic toxicity of this compound having been determined on mongrel albino mice and assessed by the Berns method. Acute toxicity implies single administration of the compound, while chronic toxicity means its multiple administration (sevenfold daily administration in the experiments under consideration). 13-(1-oxo-2,2,6,6-tetramethylpiperylidenyl-4)hydrazone rubomycin hydrochloride was administered intraperitoneally in physiological saline, the concentration of the compound in the saline being approximately 0.1 percent. There were determined the median lethal dose ($LD_{50}$) and maximum tolerance dose (MTD). The experimental evidence of the toxicity of the compound being claimed versus rubomycin and rubidazone are tabulated hereinbelow.

Antitumor activity of the compound was found experimentally on induced models of leukoses La, P-388, L-1210 inoculated on mice $BDF_1$ and on solid tumor (viz, Shvets's erythromyelosis) in rats. In all cases the compound being claimed and the known ones (rubomycin and rubidazone) were applied as a solution in physiological saline and were administered intraperitoneally, the administration was started the day after inoculation of the tumors. The doses of the compound being claimed and of rubomycin were equitoxic on all the models. On the model of leukosis La the compound being claimed was administered daily in a dose of 5 mg/kg for 7 days, while rubomycin was given according to the same schedule in a dose of 0.5 mg/kg. Leukemia P-388 was treated with the compound being claimed given in a dose of 15 mg/kg administered 7 times every 72 hours. Rubomycin was administered in a dose of 1.4 mg/kg on the same schedule. Rubidazone was administered daily for 9 days in a dose of 4 mg/kg. (cf. Cancer Treatment Reports, v. 63, No. 5, issued May, 1979; "Structure-Activity Relationships Among Daunorubicin and Adriamycin Analogs" by D. W.

Henry, pp. 845 through 848). Shvets's erythromyelosis was treated with the compound being claimed, by administering a dose of 14 mg/kg 7 times every 72 hours, while rubomycin was administered in a dose of 1.8 mg/kg on the same schedule. Leukemia L-1210 was treated with the compound being claimed, by administering in a dose of 20 mg/kg, a total of four injections being made at six-day intervals. Rubomycin was administered in a dose of 2.8 mg/kg on the same schedule, while rubidazone was administered in a maximum tolerance dose of 1.5 mg/kg daily for 9 days (cf. 9th International Congress of Chemotherapy, Abstracts published in 1975, London; "Antitumor Activity of Daunorubicin Derivatives", By G. Jolles, R. Maral, M. Messer, G. Ponsinet, pp. 63 through 65). It ought to be noted that in the abovementioned experiments leukemia L-1210 was inoculated with leukemic cells taken in an amount of $10^5$, whereas in antitumorigenic activity experiments with rubidazone leukemia L-1210 was inoculated with a much lesser number of cells, viz, $10^3$. However, inoculation with a lesser number of leukemic cells provides for more favourable conditions for chemotherapy of the disease with the use of any antitumor agent, rubidazone inclusive (cf. the preceding reference).

The criterion of antitumor activity on models P-388 and L-1210 was assumed a percentage increase of the lifespan of the treated animals, as compared to the control animals, which is calculated by the formula:

$$\overline{L} = \frac{L_{test}}{L_{cont.}} \cdot 100 - 100,$$

where
$\overline{L}$ is a percentage increase of the lifespan of the treated animals as against the control animals;
$L_{test.}$ is the lifespan of the animals in the test (treated) group;
$L_{cont.}$ is the lifespan of the animals in the control (untreated) group.

The criterion of antitumor activity on leukosis model La was the kinetic criterion (H) which is in fact the factor by which the process of leukosis in inhibited as a result of treatment with the compound being claimed and with rubomycin, as compared to the control.

The activity of the remedial compound against Shvets's erythromyelosis was assessed by the percentage inhibition of the growth of tumors in the groups of treated animals versus the control ones.

It is evident from the above table that both acute and chronic toxicity of the compound being claimed is much lower than that of the compounds tested in parallel.

The compound being claimed extends the lifespan of animals inoculated with experimental leukemia P-388 as compared to the effect of rubomycin and rubidazone, and does so in the case of leukemia L-1210 as compared to the effect of rubomycin. As to the case of treating leukemia L-1210 with rubidazone the test conditions, as it has been said hereinbefore, were much milder than in the experiment under consideration (i.e., inoculation was made with an amount of cells 100 times less than in the present test, and treatment was applied daily rather than once every six days as in the test being described). Hence a percentage increase in lifespan of the test animals was found amounting to 90 (the respective percentage for the compound being claimed is found to be 76 as tabulated above). On the other hand, it is quite conspicuous that rubidazone administration under the conditions of the present experiment would result in a shorter lifespan of the test animals as compared to the effect of the compound being claimed.

When used for treating Shvets's erythromyelosis the compound being claimed is found to inhibit the tumor growth by 80 percent as compared to the control, whereas rubomycin administration for this purpose is of no avail.

The drawing appended to the present Specification illustrates characteristic curves representing the weight (W) of the spleen in grams versus the time ($\tau$, in days) of development of leukosis process La in the control (curve I), with rubomycin application (curve II), and with application of the compound being claimed (curve III). As can be seen from the drawing, a sevenfold administration of the compound being claimed inhibits completely the process of leukosis (H=1.0), so that the process does not resume upon terminating the administration of the compound being claimed, whereas rubomycin is able to inhibit leukosis but incompletely and inhibition ceases as soon as rubomycin administration is discontinued.

Thus, the novel compound disclosed herein features a lower toxicity and higher antitumor activity as compared to the known compounds being compared, and is therefore of much interest for use in chemopharmaceutical industry and medicine.

What is claimed is:

1. 13-(1-Oxyl-2,2,6,6-tetramethylpiperylidenyl-4)hydrazone rubomycin hydrochloride with a paramagnetic centre, of the formula

TABLE

| Compounds | Number of administrations | | | | Increase of animals' lifespan, percent of control | | Tumor growth inhibition, percent of control |
|---|---|---|---|---|---|---|---|
| | MTD,mg/kg | | $LD_{50}$,mg/kg | | | | Shvets' erythromyelosis |
| | 1 | 7 | 1 | 7 | P-388 | L-1210 | |
| Compound being claimed (Ruboxyl) | 20 | 5 | 44 | 8 | 153.0 | 76.0 | 80.0 |
| Rubomycin | 3.7 | 0.5 | 5.5 | 1.4 | 68.0 | 25.0 | 0.0 |
| Rubidazone | | | 1.5 | 4.4* | 92 ± 39 | 90.0 | |

*$LD_{50}$ for rubidazone is determined after fivefold administration (cf. C.R.Acad. Sc. Paris, No. 1, issued July 10, 1972. "Etude de l'activite antitumorale d'un nouvel antibiotique senti-synthetique: la rubidazone" by R. Maral, G. Ponsinet, G. Jolles, pp. 301 through 304).

2. A method of producing 13-(1-oxo-2,2,6,6-tetramethylpiperylidenyl-4)hydrazone rubomycin hydrochloride with a paramagnetic centre, of the formula

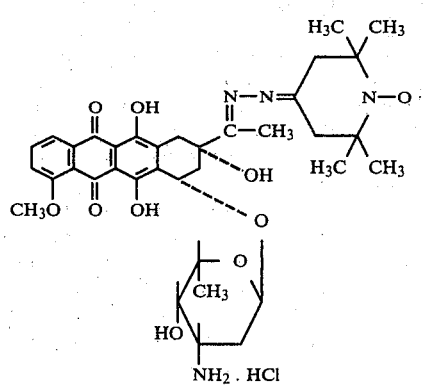

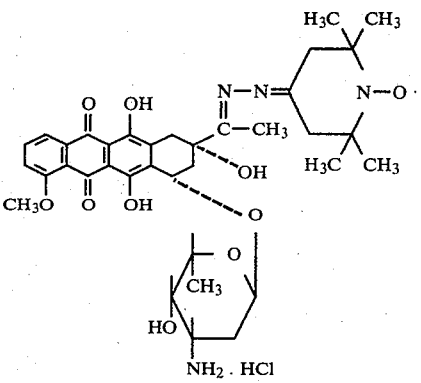

comprising treating rubomycin hydrochloride with an alkali to form the rubomycin base, reacting said rubomycin base with 1-oxo-2,2,6,6-tetramethyl-piperidone-4-hydrazone in a respective molar ratio of 1:1:5 to 2 in a chloroform-methanol medium with a respective volumetric ratio of 8:1 in the presence of acetic acid in a fourfold molar excess with respect to said rubomycin base at 20° to 25° C., separating the formed precipitate, treating the solution remaining after separation and containing the reaction product with an alcoholic solution of hydrogen chloride in a twofold molar excess with respect to said rubomycin base and precipitating the end product with diethyl ether.

* * * * *